(12) United States Patent
Lane et al.

(10) Patent No.: US 8,871,781 B2
(45) Date of Patent: Oct. 28, 2014

(54) METHODS AND COMPOSITIONS FOR TREATING A SUBJECT FOR A LYMPHATIC MALFORMATION

(71) Applicant: The Board of Trustees of the Leland Stanford Junior University, Palo Alto, CA (US)

(72) Inventors: Alfred T. Lane, Los Altos, CA (US); David Berk, St. Louis, MO (US); Anna L. Bruckner, Centennial, CO (US); Glenda Louise Swetman, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 32 days.

(21) Appl. No.: 13/689,398

(22) Filed: Nov. 29, 2012

(65) Prior Publication Data

US 2013/0345232 A1  Dec. 26, 2013

Related U.S. Application Data (60) Provisional application No. 61/565,403, filed on Nov. 30, 2011.

(51) Int. Cl.
| | | |
|---|---|---|
| *A61K 31/415* | (2006.01) | |
| *A61K 31/496* | (2006.01) | |
| *A61K 31/505* | (2006.01) | |
| *A61K 31/522* | (2006.01) | |
| *A61K 31/519* | (2006.01) | |
| *A61K 45/06* | (2006.01) | |
| *C07D 487/04* | (2006.01) | |
| *A61K 31/5025* | (2006.01) | |

(52) U.S. Cl.
CPC ............ *C07D 487/04* (2013.01); *A61K 31/522* (2013.01); *A61K 31/519* (2013.01); *A61K 45/06* (2013.01); *A61K 31/5025* (2013.01)
USPC ............................ 514/284; 514/341; 514/403

(58) Field of Classification Search
CPC .. A61K 31/415; A61K 31/496; A61K 31/505
USPC ........................................ 514/284, 341, 403
See application file for complete search history.

(56) References Cited

U.S. PATENT DOCUMENTS

| | | |
|---|---|---|
| 5,250,534 A | 10/1993 | Bell et al. |
| 2007/0111983 A1 | 5/2007 | Fong |
| 2009/0239883 A1 | 9/2009 | Butrous et al. |

OTHER PUBLICATIONS

Colbert et al. "Lymphatic malformations of the head and neck—current concepts in management". British Journal of Oral and Maxillofacial Surgery 51 (2013) 98-2012.*
Swetman; et al., "Sildenafil for Severe Lymphatic Malformations" The New England Journal of Medicine (Jan. 2012), 366(4):384-386.

* cited by examiner

*Primary Examiner* — Renee Claytor
(74) *Attorney, Agent, or Firm* — Bozicevic, Field & Francis LLP; Bret E. Field

(57) ABSTRACT

Methods of treating lymphatic malformations using a phosphodiesterase type 5 inhibitor are provided. Pharmaceutical compositions and kits comprising phosphodiesterase type 5 inhibitors are also provided.

5 Claims, 3 Drawing Sheets

METHODS AND COMPOSITIONS FOR TREATING A SUBJECT FOR A LYMPHATIC MALFORMATION

CROSS-REFERENCE TO RELATED APPLICATIONS

Pursuant to 35 U.S.C. §119 (e), this application claims priority to the filing date of the U.S. Provisional Patent Application Ser. No. 61/565,403, filed Nov. 30, 2011, the disclosure of which is incorporated herein by reference.

GOVERNMENT RIGHTS

This invention was made with Government support under contracts RR025742 and TR000093 awarded by the National Institutes of Health. The Government has certain rights in the invention.

INTRODUCTION

Lymphatic malformations (LMs) are congenital vascular anomalies that arise due to developmental dysplasia of the lymphatic network in utero. Although histologically benign, LMs can be progressive and may be debilitating due to obstruction or mass effect on vital functions or organs, risk for recurrent infection, and the negative psychosocial effects of disfigurement. Current treatments for LM are palliative and only partially successful, including compression, surgical resection, laser ablation, and sclerotherapy. LMs may recur, despite such treatment.

SUMMARY

Methods of treating lymphatic malformations are provided. Aspects of the methods include administering to a subject an effective amount of a phosphodiesterase type 5 inhibitor, e.g., sildenafil. Pharmaceutical compositions and kits for use in practicing methods of the invention, e.g. including phosphodiesterase type 5 inhibitors, are also provided.

Methods of the present disclosure include treating a subject for a lymphatic malformation, the methods including administering to the subject an amount of a phosphodiesterase 5 (PDE5) inhibitor effective to treat the subject for the lymphatic malformation. Target lymphatic malformations may be lymphangiomas, such as microcystic or macrocystic lymphangiomas. The subject being treated may be one that has been diagnosed with a lymphatic malformation. Subjects suitable for treatment via methods disclosed herein include mammals, e.g., humans.

The PDE5 inhibitor may have the formula:

where
$R^2$ is selected from hydrogen, alkyl, and substituted alkyl; each $R^3$ is independently selected from sulfonyl, aminosulfonyl, sulfonylamino, alkoxy, substituted alkoxy, hydroxyl, acyl, acylamino, and aminoacyl; n is a number from zero to three; and $R^{Q2}$ is present or not present depending on the valence and is selected from hydrogen, amino, substituted amino, alkyl, and substituted alkyl. In some embodiments, the PDE5 inhibitor is selected from vardenafil, tadalafil, dasantafil, dipyridamole, 2-(2-Methylpyridin-4-yl)methyl-4-(3,4,5-trimethoxyphenyl)-8-(pyrimidin-2-yl)methoxy-1,2-dihydro-1-oxo-2,7-naphthyridine-3-carboxylic acid methyl ester hydrochloride, (methyl 2-(4-aminophenyl)-1,2-dihydro-1-oxo-7-(2-pyridylmethoxy)-4-(3,4,5-trimeth-oxy-phenyl)-3-isoquinoline carboxylate sulfate), sildenafil, sildenafil derivatives and analogs, vesnarinone, zaprinast, and mixtures thereof.

The amount of PDE5 inhibitor administered to the subject may vary, ranging in some instances from 0.5 mg/kg/day to 30 mg/kg/day, such as 5 mg/kg/day to 25 mg/kg/day, including 10 mg/kg/day to 20 mg/kg/day, e.g., 12.5 to 17.5 mg/kg/day.

Routes of administration may vary. In some embodiments, the PDE5 inhibitor is enterally, e.g., orally, administered to the subject. In some embodiments, the PDE5 inhibitor is administered to the subject by topically applying a composition including the PDE5 inhibitor to the skin of the subject.

Where desired, the methods disclosed herein may further include administering an effective amount of a second lymphatic malformation treatment to the subject in combination with the PDE5 inhibitor. The second lymphatic malformation treatment may vary, where second lymphatic malformation treatments of interest include, but are not limited to, PDE5 inhibitors, selenium, mTOR inhibitors, beta blockers, anti-inflammatory agents, antibiotics, and combinations thereof.

In certain instances, the methods disclosed herein may further include treating a subject for a lymphatic malformation by performing compression, surgical resection, laser ablation, or sclerotherapy to the subject in combination with administration of a PDE5 inhibitor.

Aspects of the invention also include pharmaceutical compositions including a PDE5 inhibitor (e.g., as described above) and a second lymphatic malformation treatment (e.g., as described above), where the compositions may be configured for use in methods such as those summarized above.

Also provided are kits including an effective amount of a PDE5 inhibitor as an active agent, and instructions for using the composition to treat a lymphatic malformation in a subject in need thereof.

These and other aspects will be apparent to the ordinarily skilled artisan upon reviewing the present disclosure.

BRIEF DESCRIPTION OF THE DRAWINGS

The invention may be best understood from the following detailed description when read in conjunction with the accompanying drawings. Included in the drawings are the following figures.

DETAILED DESCRIPTION

Methods of treating lymphatic malformations using a PDE5 inhibitor are provided. Pharmaceutical compositions and kits configured for use in methods of the invention, e.g., including PDE5 inhibitors, are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a lymphatic malformation" includes a plurality of such lymphatic malformations and reference to "the pharmaceutical composition" includes reference to one or more pharmaceutical compositions, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

It should be noted that, as is conventional in drawing some chemical structures, some of the hydrido groups are omitted from the drawn structures for clarity purposes, but should be understood to be present, e.g. where necessary to completely fill out the valence bonding of a carbon in a drawn structure.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include treating a subject for a lymphatic malformation by at least administering to the subject an effective amount of a PDE5 inhibitor. The term "lymphatic malformation," as used herein, refers to any congenital vascular anomaly, and may include lesions in locations such as the neck, armpit, in soft tissues, bones, or organs. Exemplary lymphatic malformations include, but are not limited to: Gorham syndrome, Milroy disease, lymphangioma circumscriptum, angiokeratoma, and microcystic or macrocystic lymphangiomas.

By "treatment," "treatment," or "treat" is meant that at least an amelioration of the symptoms associated with the condition afflicting the subject is achieved, where amelioration is used in a broad sense to refer to at least a reduction in the magnitude of a parameter, e.g., a symptom, associated with the condition being treated. As such, treatment includes a broad spectrum of situations ranging from slowing, delaying, or halting progression of a pathological condition and/or a related symptom, up to and including completely eliminating the condition, along with any associated symptoms. Treatment therefore includes situations where the condition, or at least a symptom associated therewith, is completely inhibited, e.g., prevented from happening, or stopped, e.g., terminated, such that the subject no longer suffers from the condition, or at least the symptoms that characterize the condition. Treatment also includes situations where the progression of the condition, or at least the progression of a symptom associated therewith, is slowed, delayed, or halted. In such cases, a subject might still have residual symptoms associated the pathological condition, but any increase in the severity or magnitude of the symptoms is slowed, delayed, or prevented. In some instances, treatment results in a least a delay in lymphatic malformation growth (i.e., a reduction in lymphatic malformation growth rate) in a subject as compared to a suitable control, where in some instances the delay may be 2% longer, e.g., 5% or longer, such as 10%, 25%, 50% or 100% or longer. In some aspects, treatment results in a decrease in the volume of a lymphatic malformation in a subject, where in some instances the decrease in volume may be 2% or more, such as 5%, 10%, 20%, 40%, 60%, 80% or 100%.

PDE5 Inhibitors

As summarized above, in practicing methods of the invention an effective amount of a PDE5 inhibitor is administered to the subject. As described below, a variety of PDE5 inhibitors may be administered in accord with the subject methods to treat a subject for a lymphatic malformation.

In some instances, the PDE5 inhibitor may be a compound of the formula:

where
R$^1$ is selected from oxo, aryl, or substituted aryl;
R$^2$ is selected from hydrogen, alkyl, and substituted alkyl;
Q$^1$ is selected from C or N;
R$^{Q1}$ is present or not present depending on the valence and is selected from hydrogen, amino, substituted amino, alkyl, and substituted alkyl;
Q$^2$ is selected from C or N;
R$^{Q2}$ is present or not present depending on the valence and is selected from hydrogen, amino, substituted amino, alkyl, and substituted alkyl; and
--- is a double bond or single bond.

The PDE5 inhibitor may be a compound of the formula:

where
R$^2$ is selected from hydrogen, alkyl, and substituted alkyl;
each R$^3$ is independently selected from sulfonyl, aminosulfonyl, sulfonylamino, alkoxy, substituted alkoxy, hydroxyl, acyl, acylamino, and aminoacyl;
n is a number from zero to three;
Q$^1$ is selected from C or N;
R$^{Q1}$ is present or not present depending on the valence and is selected from hydrogen, amino, substituted amino, alkyl, and substituted alkyl;
Q$^2$ is selected from C or N;
R$^{Q2}$ is present or not present depending on the valence and is selected from hydrogen, amino, substituted amino, alkyl, and substituted alkyl; and
--- is a double bond or single bond.

The PDE5 inhibitor may be a compound of the formula:

where
R$^2$ is selected from hydrogen, alkyl, and substituted alkyl;
each R$^3$ is independently selected from sulfonyl, aminosulfonyl, sulfonylamino, alkoxy, substituted alkoxy, hydroxyl, acyl, acylamino, and aminoacyl;
n is a number from zero to three; and
R$^{Q2}$ is present or not present depending on the valence and is selected from hydrogen, amino, substituted amino, alkyl, and substituted alkyl.

The PDE5 inhibitor may be a compound of the formula:

where
R$^{10}$ is selected from aryl, substituted aryl, piperidinyl, piperazinyl, morpholinyl, and thiomorpholinyl;
R$^{11}$ is selected from aryl, substituted aryl, piperidinyl, piperazinyl, morpholinyl, and thiomorpholinyl;
Q$^{10}$, Q$^{11}$, Q$^{12}$, and Q$^{13}$ are independently selected from hydroxyl, thiol, amino, substituted amino, and halo; and
each m is a number from one to four.

The PDE5 inhibitor may be a compound of the formula:

where
R$^{20}$ is selected from hydrogen, alkyl, substituted alkyl, and acyl; and
R$^{21}$ is selected from aryl, substituted aryl, cycloalkyl, substituted cycloalkyl, heteroaryl, substituted heteroaryl, heterocyclyl, and substituted heterocyclyl.

The PDE5 inhibitor may be a compound of the formula:

where
$R^{20}$ is selected from hydrogen, alkyl, substituted alkyl, and acyl; and
$R^{21}$ is selected from aryl, substituted aryl, cycloalkyl, substituted cycloalkyl, heteroaryl, substituted heteroaryl, heterocyclyl, and substituted heterocyclyl.

The PDE5 inhibitor may be a compound of the formula:

where
$R^{20}$ is selected from hydrogen, alkyl, substituted alkyl, and acyl; and
$R^{21a}$, $R^{21b}$, $R^{21c}$, $R^{21d}$, and $R^{21e}$ are independently selected from hydroxyl, thiol, amino, substituted amino, and halo; any of the adjacent $R^{21a}$, $R^{21b}$, $R^{21c}$, $R^{21d}$, and $R^{21e}$ can together form a heterocyclic or substituted heterocyclic ring.

In certain embodiments, the PDE5 inhibitor may be selected, without limitation, from the group consisting of: vardenafil, tadalafil, dasantafil, dipyridamole, 2-(2-Methylpyridin-4-yl)methyl-4-(3,4,5-trimethoxyphenyl)-8-(pyrimidin-2-yl)methoxy-1,2-dihydro-1-oxo-2,7-naphthyridine-3-carboxylic acid methyl ester hydrochloride, (methyl 2-(4-aminophenyl)-1,2-dihydro-1-oxo-7-(2-pyridylmethoxy)-4-(3,4,5-trimeth-oxy-phenyl)-3-isoquinoline carboxylate sulfate), sildenafil, sildenafil derivatives and analogs, vesnarinone, zaprinast, and mixtures thereof.

A given PDE5 inhibitor may be employed as a free base or a pharmaceutically acceptable derivative thereof. Any pharmaceutically acceptable derivative of the compounds disclosed herein may be used in the methods of the present disclosure, including, e.g., pharmaceutically acceptable salts.

Administration of the PDE5 Inhibitor

In the methods of the present disclosure, treating a subject for a lymphatic malformation is accomplished by at least administering an effective amount of a PDE5 inhibitor. By "effective amount" and analogous terms is meant a dosage sufficient to treat a subject for a lymphatic malformation for a given period of time. The effective amount will vary with the weight, age and physical condition of the subject, type and severity of the LM being treated, the duration of the treatment, the frequency of administration, the nature of any concurrent treatment, the pharmaceutically acceptable carrier used if any, and analogous factors.

It is expected that the dosage will fall in a relatively broad range that can be determined through routine trials. For example, in some embodiments, the dosage is not more than an amount that could be otherwise irreversibly toxic to the subject (i.e., the maximum tolerated dose). In some embodiments, the dosage ranges from 0.5 mg/kg/day or more, up to 5 mg/kg/day or more, up to 10 mg/kg/day or more, up to 12.5 mg/kg/day or more, up to 15 mg/kg/day or more, up to 17.5 mg/kg/day or more, up to 20 mg/kg/day or more, up to 25 mg/kg/day or more, or up to 30 mg/kg/day.

One factor in determining an effective amount of a PDE5 inhibitor may be a subject's weight. For certain subjects weighing 20 kg or more, an effective amount of PDE5 inhibitor may be about 15 mg to 25 mg or more. Subjects weighing less may have effective amounts that are lower. For a subject weighing 20 kg or less, for example, an effective amount may be about 5 mg to 15 mg. For a subject weighing 10 kg or less, for example, an effective amount of PDE5 inhibitor may be about 1 mg/kg.

Effective amounts may also depend upon the frequency of administration. For instance, a subject weighing 20 kg or less may be administered an effective amount of about 5 mg to 15 mg of PDE5 inhibitor, such that the total dose is about 1 mg/kg/day, 2 mg/kg/day, 3 mg/kg/day, 4 mg/kg/day or more.

PDE5 inhibitors may be administered to a subject in a single oral dose, one time a day or more for days, weeks, months, years, even as long as a subject's lifetime or as long as the subject experiences a lymphatic malformation. For example, an embodiment may include administering a given PDE5 inhibitor one time a day over a prolonged period of time, e.g., over about 1 week, e.g., over about 1-3 months, e.g., about 3 months to about 3 years or more, e.g., orally or with a medical infusion pump or similar device designed for delivery of a substance over a prolonged period.

The frequency of administration of a PDE5 inhibitor may vary depending, e.g., on one or more of the factors described above. For example, the frequency of administration of a PDE5 inhibitor may range from about 1 time per day to multiple times per day, e.g., about 2 times or more per day or as necessary to treat or otherwise control or manage a lymphatic malformation. The duration of therapy depends on the particular subject and severity of the lymphatic malformation(s) being treated and may range from as short as about 24 hours to as long as the life of the subject. For example, at least one PDE5 inhibitor may be delivered to a subject one time or more daily for months, years or even the entire lifetime of the subject.

Embodiments may include daily discrete or continuous unit doses wherein the total number of daily units may be equal to the total number of days of a month or the like, in the form of a pack. The phrases "unit dose" and "unit dosage form," as used herein, refer to physically discrete units suitable as unitary dosages for human subjects, each unit containing a predetermined quantity of drug (i.e., PDE5 inhibitor or other pharmacological agent) calculated in an amount sufficient to produce the desired effect in association with a pharmaceutically acceptable diluent, carrier or vehicle. The specifications for the unit dosage forms of PDE5 inhibitors of the present invention depend on, for example, the particular PDE5 inhibitor(s) employed and the effect to be achieved, the pharmacodynamics associated with the particular PDE5 inhibitor(s) in the subject, etc. For example, embodiments may include daily discrete or continuous unit doses wherein the total number of daily units may be equal to the total number of days of a month, e.g., in the form of a monthly pack. Such a monthly pack may include a plurality of unit dosage forms having the same or different dosages of a PDE5 inhibitor.

The PDE5 inhibitor may be administered to a subject using any convenient administration means capable of resulting in the desired treatment of the LM. Thus, the PDE5 inhibitor may be incorporated into a variety of formulations for therapeutic administration. More particularly, the PDE5 inhibitor may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the PDE5 inhibitor and other optional ingredients in that a pharmaceutically acceptable carrier may be combined with the PDE5 inhibitor without eliminating the biological or therapeutically effective activity of the PDE5 inhibitor, and is suitable for use in subjects as provided herein without undue adverse side effects (such as toxicity, irritation, allergic response, and death). Side effects are "undue" when their risk outweighs the benefit provided by the PDE5 inhibitor. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the PDE5 inhibitor employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a PDE5 inhibitor may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperiactivityal, transdermal, intracheal, intravaginal, endocervical, intrathecal, intranasal, intravesicular, in or on the eye, in the ear canal, etc., administration. In certain embodiments, a given PDE5 inhibitor may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

As noted above, embodiments may include pharmaceutical formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one PDE5 inhibitor with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological formulations suitable for oral administration in accordance with the subject invention may be present in discrete units, such as capsules, cachets, lozenges, tablets, and the like, each containing a predetermined amount of the PDE5 inhibitor; as a powder or granules; as a solution or a suspension in an pharmacological formulations may be prepared by any suitable method of pharmacy which includes, but is not limited to, bringing into association the PDE5 inhibitor and a suitable carrier (which may contain one or more optional ingredients as noted above). For example, pharmacological formulations for use with the subject invention may be prepared by uniformly and intimately admixing the PDE5 inhibitor with a liquid or finely divided solid carrier, or both, and then, if necessary, shaping the resulting mixture. For example, a tablet may be prepared by compressing or molding a powder or granules containing the PDE5 inhibitor, optionally with one or more accessory ingredients. Compressed tablets may be prepared by compressing, in a suitable machine, the PDE5 inhibitor in a free-flowing form, such as a powder or granules optionally mixed with a binder, lubricant, inert diluent, and/or surface active/dispersing agent(s). Molded tablets may be made by molding, in a suitable machine, the powdered PDE5 inhibitor moistened with an inert liquid binder.

A PDE5 inhibitor may also be administered in the form of suppositories for rectal administration of the drug. These formulations may be prepared by mixing a PDE5 inhibitor with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include a PDE5 inhibitor made into suppositories by mixing with a variety of bases such as emulsifying bases or water-soluble bases.

A PDE5 inhibitor may also be administered by intranasal, intraocular, intravaginal, and intrarectal routes including suppositories, insufflation, powders and aerosol formulations.

For example, embodiments may also include a PDE5 inhibitor in an aerosolized, atomized or nebulized vapor form, e.g., administrable via a metered dose device or nebulizer, and the like such that embodiments also include aerosolizing, vaporing or nebulizing one or more PDE5 inhibitors for administration to a subject. Accordingly, a PDE5 inhibitor may be utilized in aerosol formulation or an analogous formulation to be administered via inhalation or analogous means. The PDE5 inhibitor employed in the practice of the present invention may be formulated into pressurized acceptable propellants such as dichlorodifluoromethane, propane, nitrogen and the like.

A PDE5 inhibitor may be delivered transdermally, by a topical route, formulated as applicator sticks, solutions, suspensions, emulsions, gels, creams, ointments, pastes, jellies, paints, powders, and aerosols. For example, embodiments may include a PDE5 inhibitor in the form of a discrete patch or film or plaster or the like adapted to remain in intimate contact with the epidermis of the recipient for a period of time. For example, such transdermal patches may include a base or matrix layer, e.g., polymeric layer, in which one or more PDE5 inhibitors or other pharmacological agents are retained. The base or matrix layer may be operatively associated with a support or backing. Pharmacological formulations suitable for transdermal administration may also be delivered by iontophoresis and may take the form of an optionally buffered aqueous solution of the pharmacological compound. Suitable formulations may include citrate or bis/tris buffer (pH 6) or ethanol/water and contain a suitable amount of active ingredient.

A PDE5 inhibitor may also be delivered as microspheres for slow release in the body. For example, microspheres may be administered via intradermal injection of drug-containing microspheres, which slowly release subcutaneously (see, e.g., Rao, J. Biomater Sci. Polym. Ed. 7:623-645, 1995); as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997); the disclosures of which are incorporated herein by reference. Both transdermal and intradermal routes afford constant delivery for weeks or months.

A PDE5 inhibitor may be provided as a salt and may be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Administration of a Second Lymphatic Malformation Treatment

As noted above, in pharmaceutical dosage forms, a PDE5 inhibitor may be administered alone or in appropriate association with, as well as in combination with, other pharmaceutically active compounds termed "second lymphatic malformation treatments."

As used herein, "administered with" means that a given pharmacological agent (e.g. a PDE5 inhibitor) and at least one other adjuvant (including one or more different pharmacological agents) are administered at times sufficiently close that the results observed are indistinguishable from those achieved when the pharmacological agent and at least one other adjuvant are administered at the same point in time. The pharmacological agent and at least one other adjuvant may be administered simultaneously (i.e., concurrently) or sequentially. Simultaneous administration may be carried out by mixing a given pharmacological agent and at least one other adjuvant prior to administration, or by administering a given pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that a given pharmacological agent and at least one other adjuvant are administered at the same point in time or immediately following one another. In the latter case, the pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

The second lymphatic malformation treatment may be selected, without limitation, from the group consisting of PDE5 inhibitors, selenium, mTOR inhibitors, beta blockers, anti-inflammatory agents and other analgesics, and antibiotics. When the second lymphatic malformation is a PDE5 inhibitor, the second PDE5 inhibitor differs from the first PDE5 inhibitor in one or more respects, e.g., they may be different PDE5 inhibitors (different types), they may be the same pharmaceutical composition but may differ in dose of active agent, etc.

Selenium formulations of interest include, but are not limited to: selenate, selenomethionine, and L-selenomethionine.

mTOR inhibitors of interest include, but are not limited to: sirolimus, everolimus, rapamycin, ridaforolimus.

Beta-blockers of interest include, but are not limited to: atenolol (e.g., as sold under the brand names TENORMIN), betaxolol (e.g., as sold under the brand name KERLONE), bisoprolol (e.g., as sold under the brand name ZEBETA), carvedilol (e.g., as sold under the brand name COREG), esmolol (e.g., as sold under the brand name BREVIBLOC), labetalol (e.g., as sold under the brand name NORMODYNE), metoprolol (e.g., as sold under the brand name LOPRESSOR), nadolol (e.g., as sold under the brand name CORGARD), pindolol (e.g., as sold under the brand name VISKEN), propranolol (e.g., as sold under the brand name INDERAL), sotalol (e.g., as sold under the brand name BETAPACE), timolol (e.g., as sold under the brand name BLOCADREN), carvedilol, and the like).

Anti-inflammatory and analgesic compounds of interest include, but are not limited to: propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; and combinations of any of the foregoing.

Antibiotics of interest include, but are not limited to: tetracycline, chlortetracycline, bacitracin, neomycin, polymyxin, gramicidin, cephalexin, oxytetracycline, chloramphenicol, rifampicin, ciprofloxacin, aminosides, gentamycin, erythromycin and penicillin, quinolone, ceftazidime, and vancomycine imipeneme.

As noted above, certain embodiments may include administering an effective amount of a PDE5 inhibitor and an effective amount of at least a second lymphatic malformation treatment, e.g., concurrently administered, where the two may differ in one or more of a variety of aspects, e.g., dosage, type, route of administration, etc. For example, embodiments may include administering a PDE5 inhibitor and at least one other type of lymphatic malformation treatment to provide an enhanced therapeutic effect. By "enhanced therapeutic effect" is meant that at least the initial relief of the particular condition being treated by the PDE5 inhibitor employed occurs more quickly with a combination of the PDE5 inhibitor and at least one other lymphatic malformation treatment, as compared to the same doses of each component given alone, or that doses of one or all component(s) are below what would otherwise be a minimum effective dose (a "subMED").

Subjects

The subject methods may be applied to a variety of subjects. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects such as, but not limited to, birds, mice, rats, dogs, cats, livestock and horses. Accordingly, it is to be understood that any subject in need of treatment for lymphatic malformation according to the present disclosure is suitable.

Moreover, suitable subjects include those who have and those who have not been diagnosed as having a lymphatic malformation. In certain embodiments, the subject methods may include a diagnostic step. Individuals may be diagnosed as being in need of the subject methods using any convenient protocol suitable for use in diagnosing the presence of a lymphatic malformation, such as visual diagnosis, magnetic resonance imaging (MRI), pre- or post-birth ultrasound, physical inspection, etc. In addition, individuals may be known to be in need of the subject methods, e.g., they are suffering from a lymphatic malformation. Methods of the present disclosure may further include assessing the efficacy of the treatment protocol, which may be performed using any convenient protocol, e.g., by monitoring the rate of regression and/or progression of the lymphatic malformation (such as by using the diagnosis protocols, e.g., as described above).

In certain embodiments, a subject may be identified as having a lesion that is about 5 cm or more in any dimension. For example, a subject may be identified as having a lesion that is about 5 cm to 10 cm or more in width, depth, or height. Measurement of the size of a lesion may be achieved by any convenient means, such as by MRI, visual diagnosis, or the use of calipers. The contents of a lesion may be identified, such as by MRI. A lesion may be identified as including, e.g., about 20% or more, about 30% or more, about 40% or more, or 50% or more lymphatic tissue.

The size and/or contents of a lesion may be determined prior to treatment, during treatment, or after treatment. Lesions may be monitored such that treatment continues until a desired outcome is reached, e.g. reduction in width, volume, or diameter of 5% or more, 10% or more, or 20% or more. The subject methods may be continued until any particular treatment outcome is reached.

In certain embodiments, the subject methods of treating a subject for lymphatic malformation by at least administering to the subject an amount of a PDE5 inhibitor effective to treat the subject for the lymphatic malformation further comprise performing another lymphatic malformation treatment, non-limiting examples of which include performing compression, surgical resection, laser ablation, and/or sclerotherapy to the subject. Administering of the PDE5 inhibitor may commence after performing said treatment, concurrently with the treatment, or subsequent to the treatment. In certain embodiments, one or more treatments may be performed, with the treatments being homogeneous or heterogeneous.

Kits

Also provided are kits for practicing the subject methods. The subject kits may vary greatly in regards to the components included. Embodiments may include one or more pharmaceutical compositions, wherein one or more pharmaceutical composition comprises an effective amount of a PDE5 inhibitor as an active agent. In those embodiments that include one or more pharmaceutical compositions, one or more pharmaceutical composition may comprise an effective amount of an active agent for treating a lymphatic malformation that is not a PDE5 inhibitor. In those embodiments that include more than one pharmaceutical composition, the amount of the pharmaceutical compositions provided in a kit may be sufficient for a single application or for multiple applications. Accordingly, in certain embodiments of the subject kits a single dosage unit of at least one pharmaceutical composition may be present for a single application.

In certain other embodiments, multiple dosage units of one or more pharmaceutical compositions may be present in a kit for multiple applications. In those embodiments having multiple dosage units, such may be packaged in a single container, e.g., a single tube, bottle, vial, and the like, or one or more dosage units may be individually packaged such that certain kits may have more than one container of a pharmaceutical composition or of different pharmaceutical compositions.

A kit may include a monthly pack that includes daily discrete or continuous unit doses wherein the total number of daily units present in the monthly pack and may be equal to the total number of days of a month, e.g., a monthly pack may include a minimum of about 30 to about 90 days. The pack may include, for example daily unit doses in the form of oral dosage forms such as tablets, capsules and the like. The monthly pack may be a two or more stage pharmaceutical pack, e.g., containing at least about 30 daily unit doses in two stages. In its first stage, such a pack may include a first pharmaceutical composition or placebo, wherein the first stage includes a minimum of about 25 daily discrete or continuous doses. The second stage may include a second pharmaceutical composition equal to the remaining number of days, e.g., 5, 6 or 7 daily discrete or continuous unit doses. The first and second pharmaceutical compositions may differ in one or more respects, e.g., they may be different pharmaceutical compositions (different types), they may be the same pharmaceutical composition but may differ in dose of active agent, etc. More stages may be included in certain embodiments. Accordingly, the monthly pack may include a number of pills to be administered by a subject each day of the month wherein the pack is configured to include certain pills to be administered to a subject on certain days, where the type, dosage, etc. of the pills of the pack may vary.

Suitable means for delivering one or more pharmaceutical compositions to a subject may also be provided in a subject kit. The particular delivery means provided in a kit may be dictated by the particular pharmaceutical composition employed, as described above, e.g., the particular form of the composition such as whether the pharmaceutical composition is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intravaginal, endocervical, intrathecal, intranasal, intravesicular, on the eye, in the ear canal, intraperiactivityal, intradermal, transdermal, intracheal, etc. Accordingly, certain systems may include a suppository applicator, syringe, I.V. bag and tubing, electrode, transdermal patch or film, etc.

The subject kits may also include instructions for how to practice the subject methods. For example, instructions may include how to administer the one or more compositions provided in the kit to treat a using the composition to treat a lymphatic malformation in a subject in need thereof. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

Exemplary Embodiments

Non-limiting exemplary embodiments of the present disclosure are provided as follows:

1. A method of treating a subject for a lymphatic malformation, the method comprising: administering to the subject an amount of a phosphodiesterase 5 (PDE5) inhibitor effective to treat the subject for the lymphatic malformation.
2. The method according to 1, wherein the PDE5 inhibitor is selected from the group:

a)

wherein
  $R^1$ is selected from oxo, aryl, or substituted aryl;
  $R^2$ is selected from hydrogen, alkyl, and substituted alkyl;
  $Q^1$ is selected from C or N;
  $R^{Q1}$ is present or not present depending on the valence and is selected from hydrogen, amino, substituted amino, alkyl, and substituted alkyl;
  $Q^2$ is selected from C or N;
  $R^{Q2}$ is present or not present depending on the valence and is selected from hydrogen, amino, substituted amino, alkyl, and substituted alkyl; and
  === is a double bond or single bond;

b)

wherein
  $R^2$ is selected from hydrogen, alkyl, and substituted alkyl;
  each $R^3$ is independently selected from sulfonyl, aminosulfonyl, sulfonylamino, alkoxy, substituted alkoxy, hydroxyl, acyl, acylamino, and aminoacyl;
  n is a number from zero to three;
  $Q^1$ is selected from C or N;
  $R^{Q1}$ is present or not present depending on the valence and is selected from hydrogen, amino, substituted amino, alkyl, and substituted alkyl;
  $Q^2$ is selected from C or N;
  $R^{Q2}$ is present or not present depending on the valence and is selected from hydrogen, amino, substituted amino, alkyl, and substituted alkyl; and
  === is a double bond or single bond;

c)

wherein
  $R^2$ is selected from hydrogen, alkyl, and substituted alkyl;
  each $R^3$ is independently selected from sulfonyl, aminosulfonyl, sulfonylamino, alkoxy, substituted alkoxy, hydroxyl, acyl, acylamino, and aminoacyl;
  n is a number from zero to three; and
  $R^{Q2}$ is present or not present depending on the valence and is selected from hydrogen, amino, substituted amino, alkyl, and substituted alkyl;

d)

wherein
  $R^{10}$ is selected from aryl, substituted aryl, piperidinyl, piperazinyl, morpholinyl, and thiomorpholinyl;
  $R^{11}$ is selected from aryl, substituted aryl, piperidinyl, piperazinyl, morpholinyl, and thiomorpholinyl;

$Q^{10}$, $Q^{11}$, $Q^{12}$, and $Q^{13}$ are independently selected from hydroxyl, thiol, amino, substituted amino, and halo; and
each m is a number from one to four;

e)

wherein
$R^{20}$ is selected from hydrogen, alkyl, substituted alkyl, and acyl; and
$R^{21}$ is selected from aryl, substituted aryl, cycloalkyl, substituted cycloalkyl, heteroaryl, substituted heteroaryl, heterocyclyl, and substituted heterocyclyl;

f)

wherein
$R^{20}$ is selected from hydrogen, alkyl, substituted alkyl, and acyl; and
$R^{21}$ is selected from aryl, substituted aryl, cycloalkyl, substituted cycloalkyl, heteroaryl, substituted heteroaryl, heterocyclyl, and substituted heterocyclyl; and g)

wherein
$R^{20}$ is selected from hydrogen, alkyl, substituted alkyl, and acyl; and
$R^{21a}$, $R^{21b}$, $R^{21c}$, $R^{21d}$, and $R^{21e}$ are independently selected from hydroxyl, thiol, amino, substituted amino, and halo; any of the adjacent $R^{21a}$, $R^{21b}$, $R^{21c}$, $R^{21d}$, and $R^{21e}$ can together form a heterocyclic or substituted heterocyclic ring.

3. The method according to 1 or 2, wherein the PDE5 inhibitor is selected from vardenafil, tadalafil, dasantafil, dipyridamole, 2-(2-Methylpyridin-4-yl)methyl-4-(3,4,5-trimethoxyphenyl)-8-(pyrimidin-2-yl)methoxy-1,2-dihydro-1-oxo-2,7-naphthyridine-3-carboxylic acid methyl ester hydrochloride, (methyl 2-(4-aminophenyl)-1,2-dihydro-1-oxo-7-(2-pyridylmethoxy)-4-(3,4,5-trimethoxy-phenyl)-3-isoquinoline carboxylate sulfate), sildenafil, sildenafil derivatives and analogs, vesnarinone, zaprinast, and mixtures thereof.

4. The method according to any of 1-3, wherein the PDE5 inhibitor is administered orally.

5. The method according to any of 1-4, wherein the PDE5 inhibitor is inhaled.

6. The method according to any of 1-5, wherein the PDE5 inhibitor is administered one time or more per day.

7. The method according to any of 1-6, wherein the PDE5 inhibitor is administered three times a day.

8. The method according to any of 1-7, wherein the PDE5 inhibitor is in a controlled release formulation.

9. The method according to any of 1-8, wherein the subject weighs 20 kg or more, and the amount of PDE5 inhibitor administered to the subject is 15 mg to 25 mg.

10. The method according to any of 1-8, wherein the subject weighs 10 kg or less, and the amount of PDE5 inhibitor administered to the subject is 1 mg/kg.

11. The method according to any of 1-8, wherein the subject weighs 20 kg or less, and the amount of PDE5 inhibitor administered to the subject is 5 mg to 15 mg.

12. The method according to 11, wherein a total daily dose is 3 mg/kg/day.

13. The method according to any of 1-12, further comprising administering an effective amount of a second lymphatic malformation treatment.

14. The method according to 13, wherein the second lymphatic malformation treatment is selected from the group comprising selenium, mTOR inhibitors, beta blockers, anti-inflammatory agents, analgesics, and antibiotics.

15. The method according to 14, wherein the second lymphatic malformation treatment comprises an mTOR inhibitor, wherein the mTOR inhibitor is rapamycin.

16. The method according to 14, wherein the second lymphatic malformation treatment comprises a beta blocker, wherein the beta blocker is propranolol.

17. The method according to any of 1-16, wherein the subject has a macrocystic lymphangioma.

18. The method according to any of 1-17, wherein the subject has a microcystic lymphangioma.

19. The method according to any of 1-18, wherein the subject is a mammal.

20. The method according to any of 1-19, wherein the subject is a juvenile.

21. The method according to any of 1-20, wherein the subject has been diagnosed as having a lymphatic malformation.

22. The method according to 21, wherein the subject has been diagnosed as having a macrocystic lymphangioma.

23. The method according to 21 or 22, wherein the subject has been diagnosed using magnetic resonance imaging (MRI) or ultrasound.

24. The method according to any of 1-23, wherein the subject is identified as having a lesion that is 5 cm or more in width.

25. The method according to any of 1-24, wherein the subject is identified as having a lesion that is 10 cm or more in width.

26. The method according to 24 or 25, comprising measuring the size of the lesion by magnetic resonance imaging (MRI) or calipers.

27. The method according to any of 1-26, wherein the subject has a lymphangioma comprising 50% or more lymphatic tissue.
28. The method according to any 1-27, further comprising identifying that the subject has no contraindications for the use of a PDE5 inhibitor.
29. The method according to any of 1-28, further comprising evaluating the subject after the administration of the PDE5 inhibitor.
30. The method according to 29, wherein the evaluation comprises MRI or calipers.
31. The method according to any of 1-30, further comprising performing compression, surgical resection, laser ablation, or sclerotherapy to the subject.
32. The method according to 31, wherein the administering of the PDE5 inhibitor commences after performing compression, surgical resection, laser ablation, or sclerotherapy.
33. A pharmaceutical composition comprising (a) first lymphatic malformation treatment comprising a PDE5 inhibitor and (b) a second lymphatic malformation treatment.
34. The pharmaceutical composition of 33, wherein the PDE5 inhibitor is selected from the group:

a)

wherein
$R^1$ is selected from oxo, aryl, or substituted aryl;
$R^2$ is selected from hydrogen, alkyl, and substituted alkyl;
$Q^1$ is selected from C or N;
$R^{Q1}$ is present or not present depending on the valence and is selected from hydrogen, amino, substituted amino, alkyl, and substituted alkyl;
$Q^2$ is selected from C or N;
$R^{Q2}$ is present or not present depending on the valence and is selected from hydrogen, amino, substituted amino, alkyl, and substituted alkyl; and
═══ is a double bond or single bond;

b)

wherein
$R^2$ is selected from hydrogen, alkyl, and substituted alkyl;
each $R^3$ is independently selected from sulfonyl, aminosulfonyl, sulfonylamino, alkoxy, substituted alkoxy, hydroxyl, acyl, acylamino, and aminoacyl;
n is a number from zero to three;
$Q^1$ is selected from C or N;
$R^{Q1}$ is present or not present depending on the valence and is selected from hydrogen, amino, substituted amino, alkyl, and substituted alkyl;
$Q^2$ is selected from C or N;
$R^{Q2}$ is present or not present depending on the valence and is selected from hydrogen, amino, substituted amino, alkyl, and substituted alkyl; and
═══ is a double bond or single bond;

c)

wherein
$R^2$ is selected from hydrogen, alkyl, and substituted alkyl;
each $R^3$ is independently selected from sulfonyl, aminosulfonyl, sulfonylamino, alkoxy, substituted alkoxy, hydroxyl, acyl, acylamino, and aminoacyl;
n is a number from zero to three; and
$R^{Q2}$ is present or not present depending on the valence and is selected from hydrogen, amino, substituted amino, alkyl, and substituted alkyl;

d)

wherein
$R^{10}$ is selected from aryl, substituted aryl, piperidinyl, piperazinyl, morpholinyl, and thiomorpholinyl;
$R^{11}$ is selected from aryl, substituted aryl, piperidinyl, piperazinyl, morpholinyl, and thiomorpholinyl;
$Q^{10}$, $Q^{11}$, $Q^{12}$, and $Q^{13}$ are independently selected from hydroxyl, thiol, amino, substituted amino, and halo; and
each m is a number from one to four;

e)

wherein
$R^{20}$ is selected from hydrogen, alkyl, substituted alkyl, and acyl; and R²¹ is selected from aryl, substituted aryl, cycloalkyl, substituted cycloalkyl, heteroaryl, substituted heteroaryl, heterocyclyl, and substituted heterocyclyl;

f)

wherein
R²⁰ is selected from hydrogen, alkyl, substituted alkyl, and acyl; and
R²¹ is selected from aryl, substituted aryl, cycloalkyl, substituted cycloalkyl, heteroaryl, substituted heteroaryl, heterocyclyl, and substituted heterocyclyl; and g)

wherein
R²⁰ is selected from hydrogen, alkyl, substituted alkyl, and acyl; and
$R^{21a}$, $R^{21b}$, $R^{21c}$, $R^{21d}$, and $R^{21e}$ are independently selected from hydroxyl, thiol, amino, substituted amino, and halo; any of the adjacent $R^{21a}$, $R^{21b}$, $R^{21c}$, $R^{21d}$, and $R^{21e}$ can together form a heterocyclic or substituted heterocyclic ring.

35. The pharmaceutical composition of 33 or 34, wherein the PDE5 inhibitor is selected from vardenafil, tadalafil, dasantafil, dipyridamole, 2-(2-Methylpyridin-4-yl)methyl-4-(3,4,5-trimethoxyphenyl)-8-(pyrimidin-2-yl)methoxy-1,2-dihydro-1-oxo-2,7-naphthyridine-3-carboxylic acid methyl ester hydrochloride, (methyl 2-(4-aminophenyl)-1,2-dihydro-1-oxo-7-(2-pyridylmethoxy)-4-(3,4,5-trimethoxy-phenyl)-3-isoquinoline carboxylate sulfate), sildenafil, sildenafil derivatives and analogs, vesnarinone, zaprinast, and mixtures thereof.

36. The pharmaceutical composition of any of 33-35, wherein the pharmaceutical composition comprises 10 mg or more of the PDE5 inhibitor.

37. The pharmaceutical composition of any of 33-35, wherein the pharmaceutical composition comprises 20 mg or more of the PDE5 inhibitor.

38. The pharmaceutical composition of any of 33-37, wherein the second lymphatic malformation treatment is selected from the group comprising selenium, mTOR inhibitors, beta blockers, anti-inflammatory agents, analgesics, and antibiotics.

39. The pharmaceutical composition of any of 33-38, wherein the pharmaceutical composition is formulated for oral administration.

40. The pharmaceutical composition of any of 33-38, wherein the pharmaceutical composition is formulated for inhaled administration.

41. The pharmaceutical composition of any of 33-40, wherein the pharmaceutical composition is formulated in a controlled release formulation.

42. A kit for treating a lymphatic malformation comprising:
    (a) a composition comprising an effective amount of a phosphodiesterase 5 (PDE5) inhibitor as an active agent; and
    (b) instructions for using the composition to treat a lymphatic malformation in a subject in need thereof.

43. The kit according to 42, further comprising an effective amount of a second active agent for treating a lymphatic malformation.

44. The kit according to 43, wherein the composition comprises the second active agent.

45. The kit according to any of 42-44, wherein the kit comprises a plurality of compositions that are present in separate containers.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Figure 1:
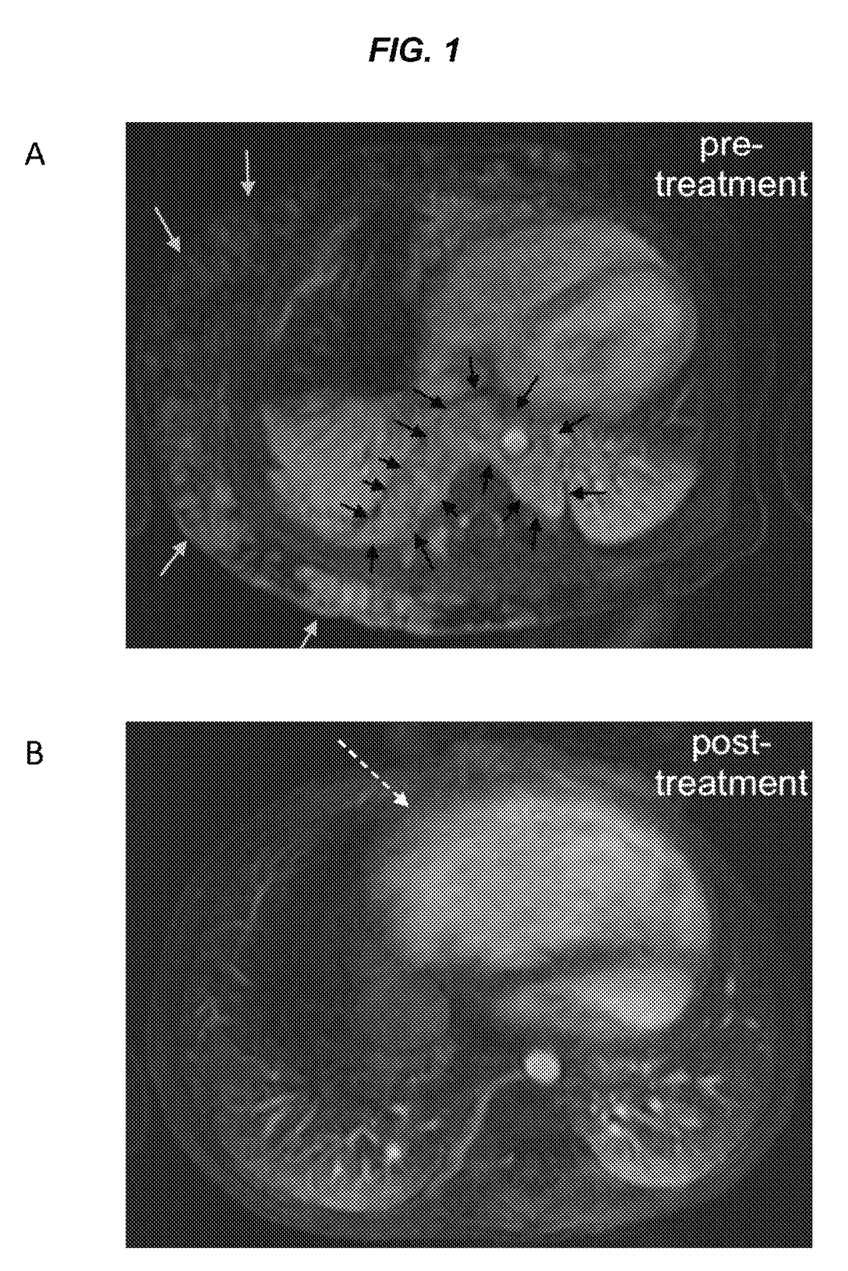
FIG. 1, Panels A-B depict pre- and post-treatment magnetic resonance imaging (MRI) contrast-enhanced images of a subject with a lymphatic malformation treated in accord with the subject methods. (Panel A) Magnetic resonance imaging of the index patient before treatment with a PDE5 inhibitor (sildenafil) demonstrates an enhancing, low-flow malformation. Transverse section of the chest shows involvement of the subcutaneous chest wall (white arrows) with pleural, paravertebral, mediastinal and para-aortic involvement (black arrows) without extension into bone. (Panel B) After therapy, near complete resolution of the malformation is seen. Contrast highlights the heart with right ventricular enlargement (dashed arrow), aorta, and pulmonary vessels.

An African-American female infant was born with massive enlargement of her right chest and arm. Evaluation at 10 weeks of age revealed a non-pulsatile, violaceous, nodular and telangiectatic plaque affecting the right chest, axilla, and arm. Magnetic resonance imaging (MRI) demonstrated a low-flow lesion consistent with a microcystic venolymphatic malformation with pleural, mediastinal, paravertebral, and para-aortic extension (FIG. 1, Panel A). At 5 months of age, the infant developed tachypnea due to congestive heart failure and pulmonary edema. Echocardiogram revealed pulmonary hypertension (60 mm Hg above right atrial pressure) but no congenital anomalies. Computed tomography angiography did not identify pulmonary emboli or a high-flow malformation, and coagulation studies were normal. Although initial improvement was seen with diuretics, fluid restriction and supplemental oxygen, the infant's cardiorespiratory condition worsened and was complicated by severe failure to thrive. At 9 months, cardiac catheterization confirmed the diagnosis of idiopathic pulmonary hypertension and sildenafil was started (initially 0.5 mg/kg/dose TID and titrated to 0.75 mg/kg/dose TID). The malformation gradually decreased in size, and four months after starting sildenafil, skin examination demonstrated a thin, bluish plaque and redundant tissue. Cardiac MRI was performed at 20 months of age as part of a pre-transplant assessment and noted minimal residual lymphatic malformation (FIG. 1, Panel B). The post-MRI course was complicated by worsening cardiopulmonary interactions, respiratory failure and subsequent cardiac failure leading to her death. Sildenafil was not thought to play a role in her death.

Example 2

Based on the observation of marked regression in a lymphatic malformation after starting sildenafil, a pilot study to treat otherwise healthy children with LMs with sildenafil was approved by the Stanford University Human Research Protection Program (IRB). After informed consent was obtained, sildenafil (goal dose 1.0 mg/kg/dose TID) was administered to two children with disabling LMs for 12 weeks, and results are summarized in Table 1.

Sildenafil was tolerated without significant adverse effects. Both subjects elected to continue the medication due to the improvement seen in the study.

TABLE 1

Improvement of lymphatic malformations after 12 weeks of treatment with sildenafil

| Subject | Age at study initiation (months), gender | LM location(s) | MD impression of change in LM after 12 weeks of therapy* | Parent impression of change in LM after 12 weeks of therapy* | Change in LM 4 weeks after discontinuing therapy | Adverse effects |
|---|---|---|---|---|---|---|
| 1 | 12, male | Left orbit, upper and lower eyelids | Minimal | Fair | Enlargement | Loose yellow stools, not symptomatic |
| 2 | 15, female | Right upper back | Good | Good | Enlargement | None |
|  |  | Right axilla, chest | Fair | Good | Stable |  |
|  |  | Left forearm | Minimal | Good | Stable |  |

*Categories of improvement were defined as: Unchanged (0%) or larger than baseline; minimal (1%-25% reduction in size); fair (25%-50% reduction in size); good (50%-75% reduction in size); excellent (>75% reduction in size)

The LM of subject 1 obstructed input into the affected eye. Although improved eye opening and definition of the upper eyelid fold and superior palpebral sulcus was noted after 3 weeks of therapy, his upper eyelid was debulked to reduce the risk of amblyopia. A 25% improvement was noted at the end of treatment, and enlargement of the lesion was seen after stopping the medication.

Figure 2:
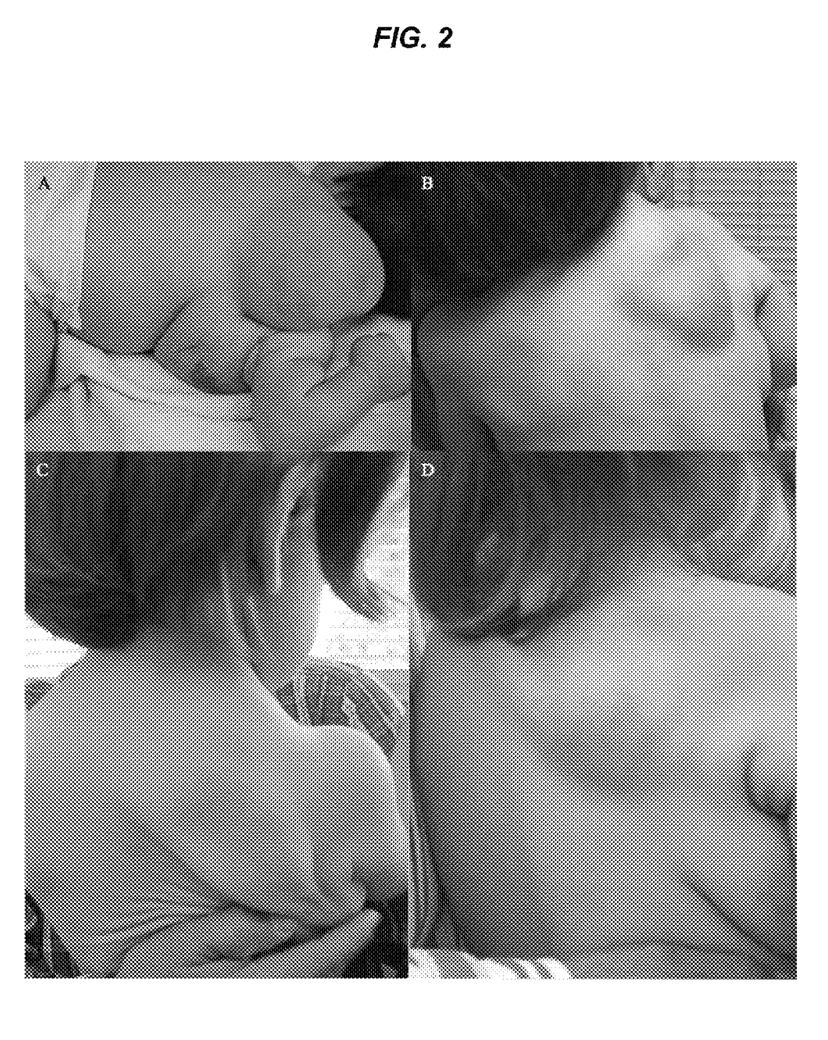
FIG. 2, Panels A-D show a subject at 9 weeks of age before any intervention (Panel A) and at 14 months of age after 5 sclerotherapy procedures (Panel B). Although improved, the LM on the back was tense and extended over the shoulder to involve the anterior clavicle. After 12 weeks of oral administration of a PDE5 inhibitor, the lymphatic malformation was soft and sagging (Panel C). 4 weeks after discontinuing the PDE5 inhibitor, mild enlargement was appreciated (Panel D).

Subject 2 had large LMs that had been diagnosed on prenatal ultrasound and had undergone several sessions of sclerotherapy with partial improvement prior to enrolling in the study (FIG. 2, Panels A-B). After 8 and 12 weeks of treatment, 50% and 75% improvement, respectively, were seen. At the 12 week visit, the large LM affecting the back appeared deflated, leaving redundant skin and tissue (FIG. 2, Panel C). Four weeks after stopping the medication, mild enlargement of the LMs was noted (FIG. 2, Panel D).

Figure 3:
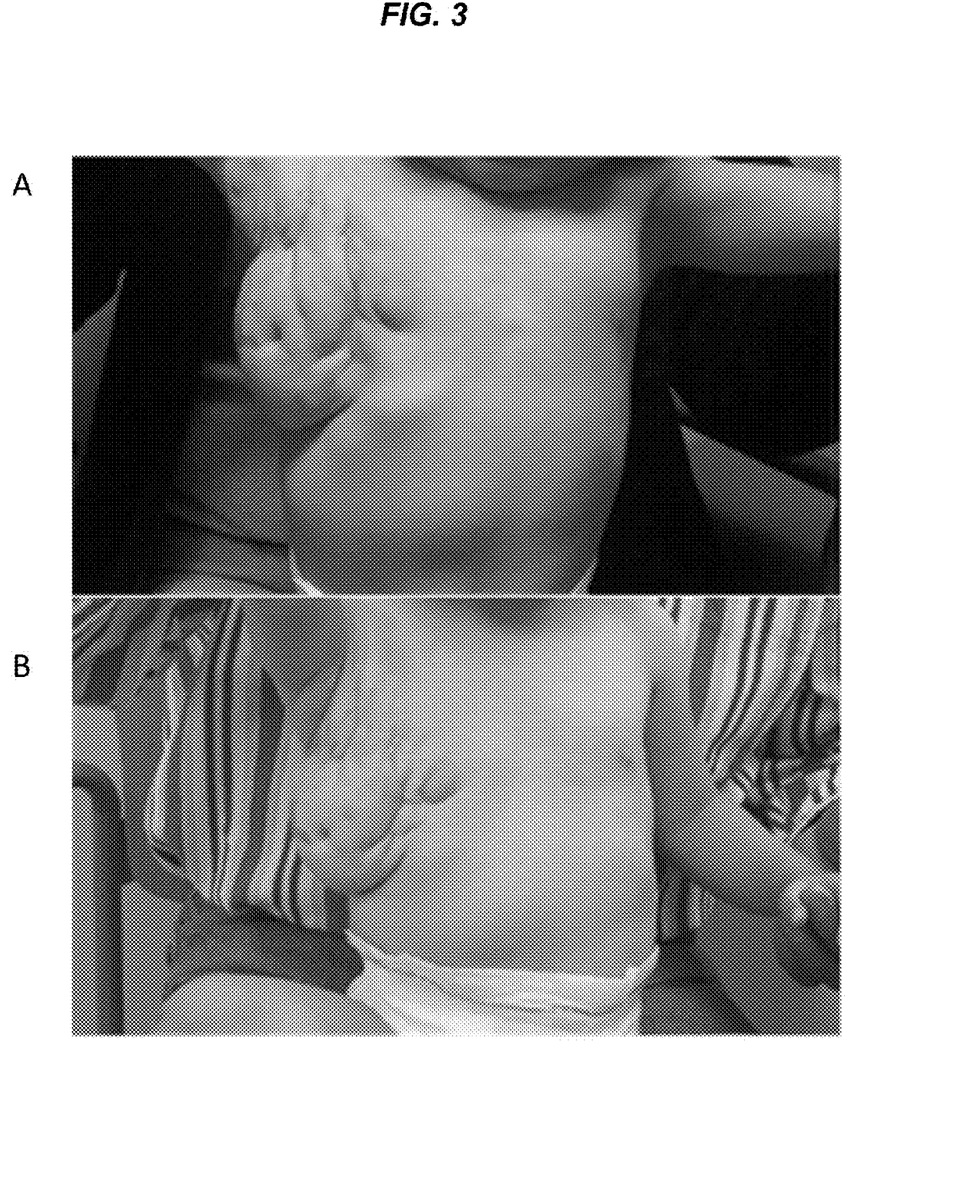
FIG. 3, Panels A-B depict pre- and post-treatment frontal views of a year old child with lymphangioma of right axilla and back. (Panel A) Prior to treatment with the PDE5 inhibitor sildenafil. (Panel B) After 12 weeks of treatment. The lesion is softer and saggier, with a reduction of 1 cm in diameter.

Subject 2 also had a large LM of right axilla (FIG. 3, Panel A). After treatment, the lesion was softer and saggier, with a volume reduction of 1 cm in diameter (FIG. 3, Panel B).

Example 3

An additional 7 subjects were enrolled into a clinical trial. Sildenafil was administered substantially as described above in Examples 1-2. Each subject had an MRI before starting sildenafil and after 20 weeks of sildenafil. Three subjects completed the 20 week trial and had the follow up MRI completed; the remaining four subjects are still undergoing the trial.

There were no adverse events associated with the sildenafil medication. The three subjects decreased the volume of the lymphatic malformation over the 20 weeks of the trial. The volume changes for the three subjects evaluated were 186 cc to 174 cc (6.45% decrease), 46.5 cc to 42.7 cc (8.17% decrease) and 56.246 cc to 51.732 cc (8.03% decrease), respectively.

Although the volume change is small it is unusual for the lymphatic malformations to shrink as the usually increase in volume over time, and it is expected that if the subjects continue to take the sildenafil the lesions will continue to shrink. Two families have refused to stop the sildenafil after 20 weeks because they thought their children are much better. Those subjects have continued the sildenafil past the 20 week trial and will be followed to understand their outcome.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject for a lymphatic malformation, the method comprising: administering to the subject an amount of sildenafil effective to treat the subject for the lymphatic malformation.

2. The method according to claim 1, wherein the sildenafil is administered orally.

3. The method according to claim 1, wherein the subject weighs 10 kg or less, and the amount of sildenafil administered to the subject is 1 mg/kg.

4. The method according to claim 1, wherein the subject is a human.

5. The method according to claim 1, further comprising performing compression, surgical resection, laser ablation, or sclerotherapy to the subject.

* * * * *